(12) United States Patent
Sakai et al.

(10) Patent No.: US 8,906,424 B2
(45) Date of Patent: Dec. 9, 2014

(54) LICORICE POLYPHENOL PREPARATION

(75) Inventors: Midori Sakai, Hyogo (JP); Toshinori Ikehara, Hyogo (JP)

(73) Assignee: Kaneka Corporation, Osaka (JP)

( * ) Notice: Subject to any disclaimer, the term of this patent is extended or adjusted under 35 U.S.C. 154(b) by 837 days.

(21) Appl. No.: 12/297,354

(22) PCT Filed: Apr. 12, 2007

(86) PCT No.: PCT/JP2007/058078
§ 371 (c)(1),
(2), (4) Date: Oct. 16, 2008

(87) PCT Pub. No.: WO2007/123044
PCT Pub. Date: Nov. 1, 2007

(65) Prior Publication Data
US 2009/0087419 A1  Apr. 2, 2009

(30) Foreign Application Priority Data

Apr. 17, 2006 (JP) .................................. 2006-112961
Jul. 21, 2006 (JP) .................................. 2006-198908

(51) Int. Cl.
| | | |
|---|---|---|
| A61K 36/00 | (2006.01) | |
| A61K 38/43 | (2006.01) | |
| A61K 36/899 | (2006.01) | |
| A61K 31/225 | (2006.01) | |
| A23D 7/01 | (2006.01) | |
| A61Q 19/00 | (2006.01) | |
| A23L 1/00 | (2006.01) | |
| A23K 1/16 | (2006.01) | |
| A23L 1/035 | (2006.01) | |
| A23D 7/005 | (2006.01) | |
| A61K 9/00 | (2006.01) | |
| A23L 1/30 | (2006.01) | |
| A61K 8/97 | (2006.01) | |
| A61K 36/484 | (2006.01) | |
| A61K 9/08 | (2006.01) | |
| A61K 9/12 | (2006.01) | |

(52) U.S. Cl.
CPC ............... *A23L 1/035* (2013.01); *A23D 7/011* (2013.01); *A61Q 19/00* (2013.01); *A23L 1/0029* (2013.01); *A23K 1/1612* (2013.01); *A61K 9/124* (2013.01); *A23D 7/0053* (2013.01); *A61K 9/006* (2013.01); *A23L 1/3002* (2013.01); *A61K 8/97* (2013.01); *A61K 36/484* (2013.01); *A23V 2002/00* (2013.01); *A61K 9/08* (2013.01)
USPC ........... 424/725; 424/94.1; 424/750; 514/547

(58) Field of Classification Search
CPC . A61K 2300/00; A61K 36/484; A61K 45/06; A61K 36/00; A61K 8/347; A61K 47/14; A23V 2002/00; A23V 2250/21; A23V 2200/318; A23V 2200/222; A61Q 19/00; A61Q 19/08; A23L 1/3002; A23L 2/52; A23L 1/035; A23L 1/3008; A23L 1/22058; A23L 1/3018; A23L 2/39
See application file for complete search history.

(56) References Cited

U.S. PATENT DOCUMENTS 5,744,187 A * 4/1998 Gaynor .......................... 426/599
2005/0118289 A1  6/2005 Ikehara et al.

FOREIGN PATENT DOCUMENTS

| EP | 1 491 204 A1 | 12/2004 |
|---|---|---|
| JP | 2204417 A | 8/1990 |
| JP | 6107532 A | 4/1994 |
| JP | 6199646 A | 7/1994 |
| JP | 2000212060 A | 8/2000 |
| JP | 2003073219 A | 3/2003 |
| KR | 10-1998-0031601 | 7/1998 |
| KR | 10-2004-0111455 | 12/2004 |
| WO | 2005/110400 A1 | 11/2005 |

OTHER PUBLICATIONS

European Search Report, corresponding to Application No. 07741514.9, dated Nov. 13, 2009.
Office Action dated Jul. 15, 2013, issued by the Korean Patent Office in Application No. 10-2008-7027902.

* cited by examiner

*Primary Examiner* — Iqbal H Chowdhury
(74) *Attorney, Agent, or Firm* — Sughrue Mion, PLLC

(57) ABSTRACT

This invention provides a highly concentrated licorice polyphenol preparation with high bioavailability. Further, this invention is intended to maintain high transparency of a composition without deterioration of the indigenous properties of an aqueous substance, even when such composition is added thereto. Such licorice polyphenol preparation comprises a hydrophobic licorice extract comprising licorice polyphenol as a primary component, medium-chain fatty acid triglyceride, and polyoxyethylene sorbitan fatty acid ester, and the ratio of the total weight of the hydrophobic licorice extract and medium-chain fatty acid triglyceride to the weight of polyoxyethylene sorbitan fatty acid ester is between 1:1 and 1:10.

20 Claims, No Drawings ial Application
cation No. PCT/JP2007/058078 filed Apr. 12, 2007, claiming priority based on Japanese Patent Application No. 2006-112961 filed Apr. 17, 2006 and Japanese Patent Application No. 2006-198908 filed Jul. 21, 2006, the contents of all of which are incorporated herein by reference in their entirety.

TECHNICAL FIELD

The present invention relates to licorice polyphenol preparations that can be used for foods and beverages, such as health food products or food with health claims (e.g., food for specified health uses or food with nutrient function claims), medical supplies, quasi-drugs, cosmetics, and the like.

BACKGROUND ART

Licorice is known as a crude drug, and a primary component of its water extract, i.e., glycyrrhizin (glycyrrhizinic acid), has excellent pharmacodynamic actions, such as anti-inflammatory action, antitumor action, and antiallergic action. Thus, it has been extensively used for food, medical supplies, cosmetics, and other applications. Since the glycyrrhizin is approximately 200 times sweeter than sucrose, it has been used as a sweetener.

Hydrophobic components of the licorice, which are extracted from the licorice or a residue of a licorice water extract with an organic solvent or the like, exhibit many useful actions, such as antioxidant action, antibacterial action, enzyme inhibitory action, antitumor action, antiallergic action, or antiviral action. Such hydrophobic components of the licorice, however, are not substantially dissolved in water or common oil, and are likely to be solidified and colored in the state of an organic solvent extract. Due to such unstable properties, use of such components is difficult.

Such difficulty has been overcome by, for example, a method wherein a fat solvent comprising an oil-soluble fatty acid ester of a polyhydric alcohol in an amount of at least 10% thereof is mixed with a hydrophobic licorice extract (WO 03/084556). However, it has been difficult to dissolve such fat composition comprising hydrophobic components of the licorice in an aqueous substance.

JP Patent Publication (kokai) No. 2-204417 (1990) discloses the preparation of an oil-in-water emulsion composition from a solution of a hydrophobic licorice flavonoid in medium-chain fatty acid triglyceride in the presence of an emulsifying agent. This invention, however, is intended to realize water dispersibility and not transparency or acid resistance.

JP Patent Publication (kokai) No. 2003-176233 proposes a composition comprising a licorice oil extract and polyglycerin lauric acid ester.

WO 2005/011672 discloses concentrated milk involving the use of a fat composition comprising hydrophobic components of licorice and fatty acid ester of glycerin as an emulsifying agent. This concentrated milk, however, is a non-transparent emulsified product and thus is not considered to be adequate for applications that require transparency.

Furthermore, EP 1249230 discloses that an administration of an oil-soluble substance to the body in a microemulsion preconcentrate form enhances the rate of systemic absorption. In this technique, the microemulsion preconcentrate means a solution of a lipophilic substance in an emulsifying agent, which forms a microemulsion. The microemulsion preconcentrate is an auto-emulsified preparation that forms submicron-order microemulsions upon contact with an aqueous medium.

DISCLOSURE OF THE INVENTION

Problems to Be Solved by the Invention

As described above, the applications of existing compositions comprising hydrophobic components of licorice have been disadvantageously limited with regard to, for example, dispersibility, transparency, heat resistance or acid resistance when such compositions have been used for aqueous substances. As a result of further study thereof, preparation of an oil-in-water emulsion composition comprising licorice polyphenol using fatty acid ester of polyglycerin as an emulsifying agent was found to be required complicate steps, such as high-pressure treatment, in order to confer transparency thereto. The present invention is intended to provide a licorice polyphenol preparation with high bioavailability, which can be prepared via a simple process. The present invention is also intended to maintain high transparency without deterioration of indigenous properties of an aqueous substance even if such preparation is added thereto.

Means for Resolving the Problems

Under the above circumstances, the present inventors have been discovered that a stable licorice polyphenol preparation could be prepared readily by combining specific components, the resulting preparation would be an auto-emulsified preparation that forms a microemulsion by contacting with an aqueous medium, and the preparation would have an anti-insolubilization effect of hydrophobic components of the licorice. These results have led to the completion of the present invention.

Specifically, the present invention is as follows.

(1) A licorice polyphenol preparation comprising a hydrophobic licorice extract comprising licorice polyphenol as a primary component, medium-chain fatty acid triglyceride, and polyoxyethylene sorbitan fatty acid ester, with the ratio of the total weight of the hydrophobic licorice extract and the medium-chain fatty acid triglyceride to the weight of polyoxyethylene sorbitan fatty acid ester being between 1:1 and 1:10.

(2) The licorice polyphenol preparation according to (1), wherein the ratio of the licorice polyphenol to the medium-chain fatty acid triglyceride is 1% to 50% by weight.

(3) The licorice polyphenol preparation according to (1) or (2), wherein fatty acid residue of the polyoxyethylene sorbitan fatty acid ester is at least one member selected from the group consisting of lauric acid, stearic acid, and oleic acid.

(4) The licorice polyphenol preparation according to any of (1) to (3), which further comprises coenzyme Q10.

(5) An emulsion composition obtained by adding water or an aqueous solution to the licorice polyphenol preparation according to any of (1) to (4).

(6) The emulsion composition according to any of (1) to (5), wherein the median diameter of an emulsion particle is 100 nm or smaller.

(7) A dry powder obtained by adding an excipient to the emulsion composition according to (5) or (6) and removing a moisture content therefrom.

(8) Food, beverage, medical supplies, quasi-drugs, cosmetics, or animal feeds comprising the licorice polyphenol preparation according to any of (1) to (4), the emulsion composition according to (5) or (6), or the dry powder according to (7).

(9) The food or medical supplies according to (8), which is a capsule preparation.

(10) The beverage according to (8), wherein the licorice polyphenol content is 10 to 200 mg per package.

(11) The beverage according to (8), wherein glabridin content is 1 to 20 mg per package.

Effects of the Invention

The present invention can provide a highly-concentrated and stable licorice polyphenol preparation. The preparation of the present invention can be mixed merely with water to result in a highly transparent emulsion composition. Accordingly, the present invention enables preparation of an aqueous substance that can effectively supply licorice polyphenol components and that has high bioavailability. Also, the emulsion composition obtained by using the preparation of the present invention has acid resistance or heat resistance and thus can apply to various uses. The licorice polyphenol preparation of the present invention can be mixed merely with water to result in a highly transparent emulsion composition, without high-pressure treatment.

BEST MODES FOR CARRYING OUT THE INVENTION

Hereafter, the present invention is described in detail.

The licorice polyphenol preparation of the present invention comprises a hydrophobic licorice extract comprising licorice polyphenol as a primary component, medium-chain fatty acid triglyceride, and polyoxyethylene sorbitan fatty acid ester. In such preparation, the ratio of the total weight of the hydrophobic licorice extract and the medium-chain fatty acid triglyceride to the weight of polyoxyethylene sorbitan fatty acid ester is between 1:1 and 1:10.

In the preparation of the present invention, Licorice as a material of the hydrophobic licorice extract may be the genus *Glycyrrhiza* of the family Fabaceae. For example, the licorice can include, but is not limited to, *Glycyrrhiza glabra* (*G. glabra*), *Glycyrrhiza uralensis* (*G. uralensis*), *Glycyrrhiza inflate* (*G. inflate*), *Glycyrrhiza eurycarpa* (*G. eurycarpa*), and *Glycyrrhiza aspera* (*G. aspera*). *G. glabra*, *G. uralensis*, and *G. inflate* are preferable, and *G. glabra* is particularly preferable.

The hydrophobic licorice extract used in the present invention is a licorice extract comprising licorice polyphenol as a primary component. The term "comprising . . . as a primary component" used herein refers, for example, that the polyphenol component is 50% by weight or more, preferably 60% by weight or more, and more preferably 80% by weight or more of the hydrophobic licorice extract. A method for obtaining the hydrophobic licorice extract is not particularly limited, and any known methods may be employed. For example, such extract may be obtained using of an organic solvent (e.g., ethanol, acetone, or ethyl acetate), from the aforementioned licorice, a milled powder thereof, or a residue of a water extract thereof. Preferably, the hydrophobic licorice extract may be obtained as a solution in the medium-chain fatty acid triglyceride by using the method disclosed in WO 03/084556 or WO 2005/011672 because the polyphenol preparation of the invention comprises the medium-chain fatty acid triglyceride as the fat component. Specifically, roots and/or stolons of the licorice may be extracted with ethanol, the medium-chain fatty acid triglyceride may be added to the resulting ethanol solution comprising the hydrophobic licorice extract prior to removing ethanol therefrom, and a medium-chain fatty acid triglyceride solution comprising the hydrophobic licorice extract may then be prepared. In such a case, the licorice polyphenol preparation of the invention may be obtained by adding a given amount of polyoxyethylene sorbitan fatty acid ester to the resulting such medium-chain fatty acid triglyceride solution, and mixing.

The hydrophobic licorice extract as a starting material for the polyphenol preparation of the present invention comprises, as a licorice polyphenol component, at least one compound selected from the group consisting of, for example, glycycoumarin, glycyrol, glycyrin, liquiritigenin, glicoricone, glabridin, glabrene, glabrol, 3'-hydroxyl-4'-O-methylglabridin, 4'-O-methylglabridin, glyurallin B, licocoumarone, gancaonin I, dehydroglyasperin D, echinatin, isolicoflavonol, dehydroglyasperin C, glyasperin B, glycyrrhisoflavanone, lupiwighteone, glyasperin D, and semilicoisoflavone B. An extract comprising at least one of glabridin, glabrene, glabrol, 3'-hydroxy-4'-O-methylglabridin, and 4'-O-methylglabridin is preferable, and an extract comprising all of these five components is particularly preferable.

Medium-chain fatty acid triglyceride used in the present invention is composed of, but is not particularly limited to, a C6-C12 fatty acid, preferably a C8-C10 saturated fatty acid, and most preferably a C8 saturated fatty acid as a primary component.

The polyoxyethylene sorbitan fatty acid ester is used as an emulsifying agent in the licorice polyphenol preparation of the present invention. Polyoxyethylene sorbitan fatty acid ester comprises a sorbitan fatty acid ester with an ethylene oxide added thereto, and is an emulsifying agent having higher hydrophilicity than the sorbitan fatty acid ester. In the invention, the fatty acid residue of the polyoxyethylene sorbitan fatty acid ester is not particularly limited. Polyoxyethylene sorbitan fatty acid ester having, as a fatty acid residue, a C14-C18 saturated or unsaturated fatty acid, such as lauric acid, stearic acid, or oleic acid, is preferably used. Esterification degree of such fatty acid residue is not particularly limited, but preferably a monoesterified fatty acid residue. A mixture of such substances may also be used. Polyoxyethylene sorbitan fatty acid ester used in the invention preferably has high hydrophilicity and HLB value thereof is preferably 10 or higher, and more preferably 14 or higher. Specific examples of preferable polyoxyethylene sorbitan fatty acid ester include polyoxyethylene sorbitan monolauric acid ester, polyoxyethylene sorbitan monostearic acid ester, and polyoxyethylene sorbitan monooleic acid ester.

In the licorice polyphenol preparation of the present invention, the ratio of the total weight (i.e., the total content) of the hydrophobic licorice extract and medium-chain fatty acid triglyceride to the weight (the content) of polyoxyethylene sorbitan fatty acid ester must be between 1:1 and 1:10. That is, polyoxyethylene sorbitan fatty acid ester needs to be used in an amount of 100 to 1,000 parts by weight relative to 100 parts by weight of the total weight of the hydrophobic licorice extract and medium-chain fatty acid triglyceride, and the preferable amount is 200 to 500 parts by weight. When the amount of the polyoxyethylene sorbitan fatty acid ester to be added is less than 100 parts by weight relative to 100 parts by weight of the total weight of the hydrophobic licorice extract and medium-chain fatty acid triglyceride, a stable water-soluble composition cannot be obtained. And, when the amount is more than 1,000 parts by weight, the substance cannot be sufficiently dissolved in the aqueous substance.

In the licorice polyphenol preparation of the present invention, the ratio of the licorice polyphenol to the medium-chain fatty acid triglyceride is preferably 1% to 50% by weight. The licorice polyphenol component used herein may be quantified as glabridin reduced value by using, for example, the methods described in the examples below.

The licorice polyphenol preparation of the present invention may also comprise other fat components, in addition to medium-chain fatty acid triglyceride, within the scope which does not affect the effects of the invention adversely. In such a case, the fat components are not particularly limited. For example, vegetable oil, such as corn oil, rapeseed oil, high-erucic rapeseed oil, soybean oil, olive oil, safflower oil, cottonseed oil, sunflower oil, rice bran oil, perilla oil, perilla seed oil, linseed oil, evening primrose oil, theobroma oil, peanut oil, palm oil, or palm kernel oil; animal oil, such as fish oil, beef tallow, lard, milk fat, or egg-yolk oil; synthetic oil; oil and fat prepared from any of such oils via separation, hydrogenation, or transesterification; and an oil mixture of any thereof may be used as such fat components.

Further, the licorice polyphenol preparation of the present invention may comprise other oil-soluble physiologically active substances. For example, fat-soluble vitamins, such as vitamins A, D, E, K, and P, coenzyme Q (ubiquinone or ubiquinol), and lipoic acid may be used as such oil-soluble physiologically active substances. Among them, inclusion of coenzyme Q, and in particular coenzyme Q10, is preferable. Coenzyme Q10 is localized in, for example, mitochondria, lysosomes, Golgi apparatus, microsomes, peroxisomes, or the cell membranes, and is a fat-soluble substance essential for maintaining functions of an organism, known to be involved in activation of ATP generation, in vivo antioxidation, and membrane stabilization as a component of an electron transportchain. It has drawn attention as a health-promoting substance recently, and is frequently used in the field of health food products or food with health claims, in addition to the field of medical supplies. The licorice polyphenol preparation of the invention can stably include not only a hydrophobic licorice extract, but also an oil-soluble physiologically active component such as coenzyme Q10. Furthermore, mixing thereof with water can result in a highly transparent aqueous solution (a microemulsion). The licorice polyphenol preparation of the invention is advantageous in such respect. The amount of the oil-soluble physiologically active substance that can be incorporated in the licorice polyphenol preparation of the invention is not particularly limited, but is selected arbitrarily within the range which does not impair stability of the resulting preparation or emulsification upon mixing thereof with water. In the case of coenzyme Q10, for example, the ratio of a licorice polyphenol content to a coenzyme Q10 content is preferably 1:10 to 10:1 by weight, from the viewpoint of stability, effects, and efficacy of a resulting preparation. Also, oil-soluble components, such as oil-soluble fragrance, essential oil, colorant, antioxidant, or specific gravity modifier, can also be incorporated in the licorice polyphenol preparation of the present application.

In addition to the hydrophobic licorice extract, medium-chain fatty acid triglyceride, and polyoxyethylene sorbitan fatty acid ester, a dye, an aroma chemical, a preservative, a starch adhesive, a pH adjuster, or another vitamin, mineral, or the like may be arbitrarily and optionally added for the purpose of stabilization of the preparations within the scope which does not impair the effects of the present invention.

The licorice polyphenol preparation of the present invention is an auto-emulsified preparation, and by mixing it with an aqueous component such as water, an emulsion composition containing licorice polyphenol (e.g., an oil-in-water emulsion composition) can be easily prepared. Preferably, the aqueous component used in such a case is water or an aqueous solution of a water-soluble component dissolved in water.

The aqueous component may be a mixture of water and a polyhydric alcohol (i.e., an aqueous polyhydric alcohol solution). Examples of a polyhydric alcohol include saccharides, such as liquid sugar, glycerin and sugar alcohol, such as sorbitol. Also, water-soluble components, such as water-soluble vitamins, including vitamin C, an organic acid, an amino acid, L-carnitine, or various salts, may be added to an aqueous component within an amount which does not influence the emulsification. The ratio of the licorice polyphenol preparation to the aqueous component for preparing the oil-in-water emulsion composition is not particularly limited, but preferably between 1:0.1 and 1:1,000 by weight.

The licorice polyphenol preparation of the present invention can be converted into an emulsion composition by merely mixing the said preparation with an aqueous component such as water with a stirrer or an agitator. Thus, any action for emulsification is not required. For further stabilization of emulsification, high-pressure emulsification or homogenization may be performed.

The resulting emulsion composition of the present invention is regulated such that a median diameter of emulsion particles is preferably 100 nm or smaller, more preferably 80 nm or smaller, and further preferably 50 nm or smaller. The median diameter of emulsion particles of the oil-in-water emulsion composition of the invention is generally about 10 nm or greater. The median diameter of emulsion particles is used as an indicator of stability of emulsification. The median diameter of emulsion particles of an emulsion having homogeneous dispersion is approximately 100 μm (i.e., 100,000 nm) or smaller. A so-called general emulsion is a cloudy solution having a median diameter between 0.1 μm to 100 μm (100 nm to 100,000 nm). When the median diameter is 100 nm or smaller, the emulsion is a substantially transparent. When the median diameter is smaller than 50 nm, the resulting solution is highly transparent.

The emulsion composition of the present invention can be prepared in the form of dry powder by adding an excipient, such as a saccharide (e.g., dextrin or lactose), a sugar alcohol (e.g., erythritol), or gum Arabic or ghatti gum, and then removing the moisture therefrom via a conventional technique, such as spray drying or lyophilization. The amount of the excipient is not particularly limited, but preferable that the ratio of the licorice polyphenol preparation to the excipient is between 1:0.2 and 1:100 by weight. The resulting dry powder can be dissolved in water, so that an aqueous solution comprising licorice polyphenol (i.e., an emulsion composition) can be easily prepared.

The licorice polyphenol preparation or the emulsion composition or dry powder obtained therefrom of the present invention may be used for food, medical supplies, quasi-drugs, cosmetics, or animal feeds as it is or as a composition comprising them. When the licorice polyphenol preparation or the emulsion composition or dry powder obtained therefrom of the present invention is ingested as a medical supply or food, it may be used to fill in a capsule as it is or mixed with a known carrier to prepare a capsule.

When the licorice polyphenol preparation of the invention or the emulsion composition or dry powder obtained therefrom is used for food, it may be added to food as it is or may be dissolved in water to prepare, for example, confectioneries, such as chewing gum, chocolate, candies, jelly, biscuits, or crackers, frozen desserts, such as ice cream or ice, noodles, such as Japanese wheat noodles, Chinese noodles, spaghetti, or instant noodles, kneaded products, such as steamed fish paste, fish sausage, or cake of pounded fish, seasonings, such as dressing, mayonnaise, or sauce, bread, ham, soup, various retort food products, or various frozen food products. Further, it may be applied to pet food or animal feed. Since the licorice polyphenol preparation of the invention is particularly advantageous in terms of transparency, acid resistance, and heat resistance in an aqueous system, or the emulsion composition or dry powder obtained therefrom, it may be preferably used for beverages, such as a soft drink, a nutrition-supplement beverage, or a beauty beverage. Examples of food and beverage products used in the invention include health food products and food with health claims (e.g., food for specified health uses and food with nutrient function claims).

The amount of the licorice polyphenol preparation of the present invention, or the emulsion composition or dry powder obtained therefrom to be added into food products and the like is not particularly limited, but for example, in beverage products, the licorice polyphenol content is preferably about 10 mg to 200 mg or the glabridin content is preferably about 1 mg to 20 mg per package (e.g., a bottle).

EXAMPLES

Hereafter, the present invention is described in more detail with reference to examples, although the invention is not limited to these examples.

<Median Diameter of Emulsified Water-Soluble Composition>

Median diameters of oil-in-water emulsion compositions or water-soluble compositions of Examples and of Comparative Examples were measured using an LB-550 (HORIBA, Ltd.).

<Evaluation of Acid and Heat Stability of Emulsified Water-Soluble Composition>

5,000 parts by weight of water or an aqueous solution of citric acid (pH 3; shown as "pH 3 solution" in the tables) was added to the oil-in-water emulsion composition or the water-soluble composition of the Examples and Comparative Examples, containing 1 part by weight of the total weight of the hydrophobic licorice extract and the medium-chain fatty acid triglyceride, followed by heating at 75° C. for 15 minutes. The median diameter was measured using LB-550 before and after heating.

Preparation Example 1

The rhizome part and stolons of the licorice (*G. glabra*, 1.0 kg, from Afghanistan) was extracted twice with 5.0 L of ethanol at 45° C. for 2 hours. Thereafter, 0.45 L of a concentrated solution was obtained via vacuum concentration. Subsequently, 0.3 L of this solution was further concentrated and treated with active carbon to obtain 123.6 g of the ethanol solution containing a hydrophobic licorice extract (containing 24.8 g of the hydrophobic licorice extract).

Preparation Example 2

The ethanol solution containing a hydrophobic licorice extract obtained in Preparation Example 1 (62.9 g) was mixed with 18.8 g of medium-chain fatty acid triglyceride (Actor M2; Riken Vitamin Co., Ltd.; fatty acid composition: C8:C10=99:1), the mixture was agitated for 1 hour at about 80° C., and ethanol was removed via vacuum concentration. The resultant of vacuum concentration (28.7 g) was filtrated by aspiration to remove insoluble fractions. The insoluble fractions were washed with hexane, and the recovered oil was added to the aforementioned filtrate. Medium-chain fatty acid triglyceride (Actor M2; 4.5 g) was added to 26.2 g of the resulting filtrate. 30.7 g of a solution of the hydrophobic licorice extract-containing the medium-chain fatty acid triglyceride (containing 8.9 g of the hydrophobic licorice extract) was obtained.

HPLC Analysis

<Preparation of HPLC Samples>

The solution of medium-chain fatty acid triglyceride containing a hydrophobic licorice extract (1 g) was dissolved in methanol for HPLC to adjust the total volume to 100 ml.

<HPLC Conditions>

Column: YMC J'sphere ODS-H80 column (4.6×250 mm)
Column temperature: 40° C.
Mobile phase: A=Aqueous 20 mM phosphoric acid solution
Mobile phase: B=Acetonitrile: methanol (50:50=v/v)
Gradient:
The percentage of mobile phase B was maintained at 50% of mobile phase A until 20 minutes after the start of analysis, followed by constantly increasing so as to reach 80% at the time point 75 minutes after the start of analysis, subsequently it was maintained at 100% up to 80 minutes after the start of analysis, and then maintained at 50% up to 100 minutes after the start of analysis.
Flow rate: 1 ml/min
Wavelength: UV 282 nm
Injected sample volume: 20 μl <Results of Analysis>

Said solution of a medium-chain fatty acid triglyceride containing a hydrophobic licorice extract contained 4.4 mg of glabrene, 30.0 mg of glabridin, 6.0 mg of glabrol, and 5.2 mg of 4'-O-methylglabridin.

Polyphenol Analysis

Polyphenol content (a flavonoid content) was measured by the Folin-Denis method using glabridin (Wako Pure Chemical Industries, Ltd.) as a reference material. As a result, the licorice polyphenol content in 1 g of the solution of medium-chain fatty acid triglyceride containing a hydrophobic licorice extract was 239.1 mg.

Example 1

Polyoxyethylene sorbitan monostearic acid ester (10 parts by weight; Sorgen TW 60; Dai-ichi Kogyo Seiyaku Co., Ltd.) was mixed with 10 parts by weight of the solution of medium-chain fatty acid triglyceride containing a hydrophobic licorice extract obtained in the Preparation Example 2 to prepare a licorice polyphenol preparation. The resulting licorice polyphenol preparation was dissolved in water so that the concentration of medium-chain fatty acid triglyceride solution containing a hydrophobic licorice extract becomes 1%, and then an oil-in-water emulsion composition containing licorice polyphenol was obtained. The particle diameter of the resulting composition was measured, and acid stability and heat stability were evaluated. The results thereof are summarized in Table 1.

Example 2

Polyoxyethylene sorbitan monooleic acid ester (20 parts by weight; Sorgen TW 80; Dai-ichi Kogyo Seiyaku Co., Ltd.) was mixed with 10 parts by weight of the solution of a medium-chain fatty acid triglyceride containing a hydrophobic licorice extract obtained in the Preparation Example 2 to prepare the licorice polyphenol preparation. The resulting licorice polyphenol preparation was dissolved in water to adjust the concentration of the solution of a medium-chain triglyceride containing a hydrophobic licorice extract to 1% to obtain an oil-in-water emulsion composition containing licorice polyphenol. The particle diameter of the resulting composition was measured, and acid stability and heat stability were evaluated. The results thereof are summarized in Table 1.

Example 3

Polyoxyethylene sorbitan monostearic acid ester (50 parts by weight; Sorgen TW 60) was mixed with 10 parts by weight of the solution of a medium-chain fatty acid triglyceride containing a hydrophobic licorice extract obtained in the Preparation Example 2 to prepare the licorice polyphenol preparation. The resulting licorice polyphenol preparation was dissolved in water to adjust the concentration of the solution of a medium-chain triglyceride containing a hydrophobic licorice extract to 1% to obtain an oil-in-water emulsion composition containing licorice polyphenol. The particle diameter of the resulting composition was measured, and acid stability and heat stability were evaluated. The results thereof are summarized in Table 1.

Example 4

Polyoxyethylene sorbitan monolauric acid ester (100 parts by weight; Sorgen TW 20; Dai-ichi Kogyo Seiyaku Co., Ltd.) was mixed with 10 parts by weight of the solution of a medium-chain fatty acid triglyceride containing a hydrophobic licorice extract obtained in the Preparation Example 2 to prepare the licorice polyphenol preparation. The resulting licorice polyphenol preparation was dissolved in water to adjust the concentration of the solution of a medium-chain triglyceride containing a hydrophobic licorice extract to 1% to obtain an oil-in-water emulsion composition containing licorice polyphenol. The particle diameter of the resulting composition was measured, and acid stability and heat stability were evaluated. The results thereof are summarized in Table 1.

Example 5

Polyoxyethylene sorbitan monooleic acid ester (55 parts by weight; Sorgen TW 80) and 1 part by weight of coenzyme Q10 (Kaneka Corporation) were mixed with 10 parts by weight of the solution of a medium-chain fatty acid triglyceride containing a hydrophobic licorice extract obtained in the Preparation Example 2 to prepare the licorice polyphenol preparation. The resulting licorice polyphenol preparation was dissolved in water to adjust the concentration of the solution of a medium-chain triglyceride containing a hydrophobic licorice extract to 1% to obtain an oil-in-water emulsion composition containing licorice polyphenol. The particle diameter of the resulting composition was measured, and acid stability and heat stability were evaluated. The results thereof are summarized in Table 1.

Example 6

Polyoxyethylene sorbitan monooleic acid ester (60 parts by weight; Sorgen TW 80) and 2 parts by weight of coenzyme Q10 (Kaneka Corporation) were mixed with 10 parts by weight of the solution of a medium-chain fatty acid triglyceride containing a hydrophobic licorice extract obtained in the Preparation Example 2 to prepare the licorice polyphenol preparation. The resulting licorice polyphenol preparation was dissolved in water to adjust the concentration of the solution of a medium-chain triglyceride containing a hydrophobic licorice extract to 1% to obtain an oil-in-water emulsion composition containing licorice polyphenol. The particle diameter of the resulting composition was measured, and acid stability and heat stability were evaluated. The results thereof are summarized in Table 1.

TABLE 1

Formulation (%) and results of stability evaluation of oil-in-water emulsion composition

| | | Example 1 | Example 2 | Example 3 | Example 4 | Example 5 | Example 6 |
|---|---|---|---|---|---|---|---|
| Formulation | Solution of medium-chain fatty acid triglyceride containing hydrophobic licorice extract | 1 | 1 | 1 | 1 | 1 | 1 |
| | Polyoxyethylene sorbitan monolauric acid ester (Sorgen TW20) | | | | 10 | | |
| | Polyoxyethylene sorbitan monostearic acid ester (Sorgen TW60) | 1 | | 5 | | | |
| | Polyoxyethylene sorbitan monooleic acid ester (Sorgen TW80) | | 2 | | | 5.5 | 6 |
| | Coenzyme Q10 | | | | | 0.1 | 0.2 |
| | Water | 98 | 97 | 94 | 89 | 93.4 | 92.8 |
| | Total | 100 | 100 | 100 | 100 | 100 | 100 |
| Polyphenol content in oil-in-water emulsion composition (%) | | 0.24 | 0.24 | 0.24 | 0.24 | 0.24 | 0.24 |
| Glabridin content in oil-in-water emulsion composition (%) | | 0.03 | 0.03 | 0.03 | 0.03 | 0.03 | 0.03 |
| Median diameter in oil-in-water emulsion composition (nm) | | 43.0 | 18.3 | 16.4 | 29.9 | 16.3 | 15.7 |
| Stability evaluation/ median diameters before and after heating | Addition of water (nm) | 48.0 | 18.9 | 12.1 | 13.5 | 11.2 | 12.7 |
| | Same as above 75° C. × 15 min (nm) | 50.2 | 18.4 | 13.3 | 16.5 | 16.7 | 13.9 |
| | Addition of pH 3 solution (nm) | 44.2 | 20.9 | 12.0 | 22.8 | 14 | 13.7 |
| | Same as above 75° C. × 15 min (nm) | 70.0 | 24.5 | 13.4 | 19.9 | 15.7 | 16.2 |

Example 7

Preparation of Soft Capsule

Polyoxyethylene sorbitan monooleic acid ester (50 parts by weight; Sorgen TW 80) was mixed with 10 parts by weight of the solution of a medium-chain fatty acid triglyceride containing a hydrophobic licorice extract obtained in the Preparation Example 2 to prepare a licorice polyphenol preparation. The resulting licorice polyphenol preparation was injected into a gelatin coating using a rotary soft capsule manufacturing apparatus to obtain soft capsules (internal volume: 350 mg). Each capsule contained 0.3 mg of glabrene, 1.8 mg of glabridin, 0.4 mg of glabrol, and 0.3 mg of 4'-O-methylglabridin (total amount: 2.8 mg; content: 0.8% by weight).

Example 8

Preparation of Beverage

A soft drink product comprising licorice polyphenol and coenzyme Q10 was prepared in accordance with the following formulation.

<Formulation>

| | |
|---|---|
| Sugar | 10 parts by weight |
| Citric acid (anhydrous) | 0.2 parts by weight |
| Trisodium citrate | 0.02 parts by weight |
| Water | 87.28 parts by weight |
| Oil-in-water emulsion composition containing licorice polyphenol prepared in the Example 6 | 2.4 parts by weight |
| Orange flavor | 0.1 parts by weight° |

<Preparation Method>

Sugar, citric acid, and trisodium citrate were dissolved in water, and the oil-in-water emulsion composition containing licorice polyphenol prepared in the Example 6 and orange flavor were added thereto. Further, the resultant was sterilized in a water bath at the starting temperature of 70° C. for 20 minutes and then cooled in water to obtain a soft drink product containing licorice polyphenol and coenzyme Q10.

Comparative Example 1

Polyoxyethylene sorbitan monostearic acid ester (10 parts by weight; Sorgen TW60) was added to 20 parts by weight of the solution of a medium-chain fatty acid triglyceride containing a hydrophobic licorice extract obtained in the Preparation Example 2. After mixing, the resultant was left standing for a while and then separated.

Comparative Example 2

Polyoxyethylene sorbitan monostearic acid ester (10 parts by weight; Sorgen TW60) was mixed with 50 parts by weight of the solution of a medium-chain fatty acid triglyceride containing a hydrophobic licorice extract prepared in the Preparation Example 2. However, theses substances could not be sufficiently mixed and a homogeneous solution could not be attained.

Comparative Example 3

Polyoxyethylene sorbitan monostearic acid ester (10 parts by weight; Sorgen TW60) was added to 100 parts by weight of the solution of a medium-chain fatty acid triglyceride containing a hydrophobic licorice extract obtained in the Preparation Example 2. However, these components were not satisfactorily mixed and a homogeneous solution could not be attained.

Comparative Example 4

Polyoxyethylene sorbitan monooleic acid ester (10 parts by weight; Sorgen TW80) was mixed with 20 parts by weight of the solution of a medium-chain fatty acid triglyceride containing a hydrophobic licorice extract obtained in the Preparation Example 2. Thereafter, the mixture was left standing for a while and then separated.

Comparative Example 5

Polyoxyethylene sorbitan monooleic acid ester (10 parts by weight; Sorgen TW80) was mixed with 50 parts by weight of the solution of a medium-chain fatty acid triglyceride containing a hydrophobic licorice extract obtained in the Preparation Example 2. However, these substances could not be sufficiently mixed and a homogeneous solution could not be attained.

Comparative Example 6

Polyoxyethylene sorbitan monooleic acid ester (10 parts by weight; Sorgen TW80) was mixed with 100 parts by weight of the solution of a medium-chain fatty acid triglyceride containing a hydrophobic licorice extract obtained in the Preparation Example 2. However, these substances could not be sufficiently mixed and a homogeneous solution could not be attained.

Comparative Example 7

Decaglycerin monolauric acid ester (90 parts by weight; ML-750; Sakamoto Yakuhin Kogyo Co., Ltd.) was added to 50 parts by weight of the ethanol solution containing a hydrophobic licorice extract of the Preparation Example 1 (containing about 10 parts by weight of the hydrophobic licorice extract), the resultant was dissolved in ethanol, and vacuum concentration was carried out to remove ethanol by distillation to obtain a composition comprising a licorice oil extract. Water was added in an amount of 100 parts by weight relative to 15 parts by weight of the resulting composition comprising a licorice oil extract to prepare an aqueous solution containing licorice polyphenol. In order to evaluate acid stability and heat stability, 50 parts by weight of pH 3 solution was added to 1 part by weight of the aqueous solution containing licorice polyphenol, and was heated at 75° C. for 15 minutes. The median diameter of the water-soluble composition was measured using LB-550 before and after heating. The median diameter was 66.5 nm before heating and 139.6 nm after heating.

Comparative Example 8

One part by weight of the solution of a medium-chain fatty acid triglyceride containing a hydrophobic licorice extract of Preparation Example 2 was mixed with 5 parts by weight of sucrose stearic acid ester (DK ester SS; Dai-ichi Kogyo Seiyaku Co., Ltd.) as an emulsifying agent as an oil phase, and heated at 60° C. to completely dissolve them. Further, 94 parts by weight of water was heated at 60° C. as an aqueous phase. Subsequently, the aqueous phase was added to the oil phase with stirring, and was homogenized using a Nanomizer II (Yoshida Machinery, Co. Ltd.) at an emulsifying pressure of 100 MPa ten times to prepare an oil-in-water emulsion composition containing licorice polyphenol. The particle diameter of the resulting composition was measured, and the results are shown in Table 2. Subsequently, evaluation of acid stability and heat stability of the oil-in-water emulsion composition was attempted. Upon addition of water and an aqueous citric acid solution (pH 3 solution), however, the emulsification was destroyed, and the solution was separated. Thus, diameters of emulsified particles could not be measured.

TABLE 2

Formulation (%) and median diameter of emulsion
particles of oil-in-water emulsion composition

| | | Comparative Example 8 |
|---|---|---|
| Formulation | Solution of medium-chain fatty acid triglyceride containing hydrophobic licorice extract | 1 |
| | Sucrose stearic acid ester (DK ester SS) | 5 |
| | Water | 94 |
| | Total | 100 |
| Polyphenol content of oil-in-water emulsion composition (%) | | 0.24 |
| Glabridin content of oil-in-water emulsion composition (%) | | 0.03 |
| Median diameter of emulsion particles of oil-in-water emulsion composition (nm) | | 1247.7 |

Comparative Example 9

The solution of a medium-chain fatty acid triglyceride containing the hydrophobic licorice extract of Preparation Example 2 (5 parts by weight) and 10 parts by weight of decaglycerin monolauric acid ester (ML-750; Sakamoto Yakuhin Kogyo Co., Ltd.) were heated at 60° C., and dissolved completely. The resulting licorice polyphenol solution was added to 85 parts by weight of water at 60° C., and stirred using a magnetic stirrer. However, a homogeneous emulsion could not be obtained. Consequently, an oil-in-water emulsion composition containing the licorice polyphenol was prepared using a Nanomizer II (Yoshida Machinery, Co. Ltd.) at an emulsifying pressure of 100 MPa ten times. The particle diameter of the resulting composition was measured, and acid stability and heat stability thereof were evaluated. The results thereof are summarized in Table 3.

TABLE 3

Formulation (%) of oil-in-water emulsion composition
and results of stability evaluation

| | | | Comparative Example 9 |
|---|---|---|---|
| Formulation | Solution of medium-chain fatty acid triglyceride containing hydrophobic licorice extract | | 5 |
| | Decaglycerin monolauric acid ester (ML-750) | | 10 |
| | Water | | 85 |
| | Total | | 100 |
| Polyphenol content in oil-in-water emulsion composition (%) | | | 1.20 |
| Glabridin content in oil-in-water emulsion composition (%) | | | 0.15 |
| Median diameter in oil-in-water emulsion composition (nm) | | | 13.6 |
| Stability evaluation/ median diameter before and after heating | Addition of water (nm) | | 59.5 |
| | Same as above 75° C. × 15 min (nm) | | 53.5 |
| | Addition of pH 3 water (nm) | | 84.7 |
| | Same as above 75° C. × 15 min (nm) | | 254.3 |

Example 9

Dry powder of an emulsion composition comprising a licorice polyphenol was prepared in accordance with the following formulation. Relative to 180 parts by weight of water, 4 parts by weight of the licorice polyphenol preparation prepared in the same manner as in the Example 1 and 16 parts by weight of dextrin (Pinedex #2; Matsutani Chemical Industry, Co., Ltd.) were added, and the mixture was agitated. Subsequently, water was removed from the mixture using a spray dryer (Nihon Buchi K.K.) to prepare the dry powder of the emulsion composition containing the licorice polyphenol. The resulting powder was easily dissolved in water and converted into an aqueous emulsion solution with high transparency.

The invention claimed is:

1. A licorice polyphenol preparation comprising a hydrophobic licorice extract, medium-chain fatty acid triglyceride, and polyoxyethylene sorbitan fatty acid ester, with the ratio of the total weight of the hydrophobic licorice extract and the medium-chain fatty acid triglyceride to the weight of polyoxyethylene sorbitan fatty acid ester being from 1:2 to 1:6, wherein the hydrophobic licorice extract comprises licorice polyphenols as a primary component.

2. The licorice polyphenol preparation of claim 1, wherein the ratio of the licorice polyphenol to the medium-chain fatty acid triglyceride is 1% to 50% by weight.

3. The licorice polyphenol preparation of claim 1, wherein fatty acid residue of the polyoxyethylene sorbitan fatty acid ester is at least one member selected from the group consisting of lauric acid, stearic acid, and oleic acid.

4. The licorice polyphenol preparation of claim 1, which further comprises coenzyme Q10.

5. An emulsion composition obtained by adding the licorice polyphenol preparation according to claim 1 to water or an aqueous solution.

6. The emulsion composition according to claim 5, wherein the median diameter of a emulsion particle is 100 nm or smaller.

7. A dry powder obtained by adding an excipient to the emulsion composition according to claim 5 and removing a moisture content therefrom.

8. Food, beverage, medical supplies, quasi-drugs, cosmetics, or animal feeds comprising the licorice polyphenol preparation according to claim 1.

9. Food, beverage, medical supplies, quasi-drugs, cosmetics, or animal feeds comprising the emulsion composition according to claim 5.

10. Food, beverage, medical supplies, quasi-drugs, cosmetics, or animal feeds comprising the dry powder according to claim 7.

11. The food or medical supplies according to claim 8, which is a capsule preparation.

12. The food or medical supplies according to claim 9, which is a capsule preparation.

13. The food or medical supplies according to claim 10, which is a capsule preparation.

14. The beverage according to claim 8, wherein the licorice polyphenol content is 10 to 200 mg per package.

15. The beverage of claim 9, wherein the licorice polyphenol content is 10 to 200 mg per package.

16. The beverage of claim 10, wherein the licorice polyphenol content is 10 to 200 mg per package.

17. The beverage of claim 8, wherein the licorice polyphenol preparation comprises glabridin in an amount of from 1 to 20 mg per package.

18. The beverage of claim 9, wherein the licorice polyphenol preparation comprises glabridin in an amount of from 1 to 20 mg per package.

19. The beverage of claim 10, wherein the licorice polyphenol preparation comprises glabridin in an amount of from 1 to 20 mg per package.

20. A licorice polyphenol preparation consisting essentially of a hydrophobic licorice extract, medium-chain fatty acid triglyceride, and polyoxyethylene sorbitan fatty acid ester, with the ratio of the total weight of the hydrophobic licorice extract and the medium-chain fatty acid triglyceride to the weight of polyoxyethylene sorbitan fatty acid ester being from 1:2 to 1:6, wherein the hydrophobic licorice extract comprises licorice polyphenols as a primary component.

\* \* \* \* \*